(12) United States Patent
Sherman et al.

(10) Patent No.: US 6,530,908 B1
(45) Date of Patent: Mar. 11, 2003

(54) EYE DROPPER POSITIONING DEVICE

(76) Inventors: Thomas M. Sherman, P.O. Box 32571, Phoenix, AZ (US) 85064; Theodore A. Glass, 3666 N. Miller Rd., Scottsdale, AZ (US) 85251

( * ) Notice: Subject to any disclaimer, the term of this patent is extended or adjusted under 35 U.S.C. 154(b) by 0 days.

(21) Appl. No.: 08/770,430

(22) Filed: Dec. 20, 1996

(51) Int. Cl.$^7$ .............................................. A61M 35/00
(52) U.S. Cl. ...................................... 604/300; 604/302
(58) Field of Search ................................ 604/294, 295, 604/300, 301, 302; 222/420, 421

(56) References Cited

U.S. PATENT DOCUMENTS

| | | | | |
|---|---|---|---|---|
| 3,872,866 A | | 3/1975 | Lelicoff ...................... 128/233 |
| 3,888,251 A | | 6/1975 | Harrison ..................... 128/233 |
| 4,605,398 A | * | 8/1986 | Herrick ....................... 604/302 |
| 4,685,906 A | * | 8/1987 | Murphy ....................... 604/301 |
| 4,834,727 A | | 5/1989 | Cope .......................... 604/300 |
| 4,834,728 A | | 5/1989 | McKenna ..................... 604/301 |
| 4,960,407 A | | 10/1990 | Cope .......................... 604/300 |
| 5,030,214 A | | 7/1991 | Spector ....................... 604/301 |
| 5,387,202 A | | 2/1995 | Baron ......................... 604/300 |
| 5,417,349 A | | 5/1995 | Stull .......................... 222/420 |
| 5,429,621 A | * | 7/1995 | Stahl .......................... 604/302 |
| 5,665,079 A | * | 9/1997 | Stahl .......................... 604/302 |

* cited by examiner

Primary Examiner—Ronald Stright
Assistant Examiner—David J. Cho
(74) Attorney, Agent, or Firm—The Halvorson Law Firm P.C

(57) ABSTRACT

The present invention is directed to a device to aid in the placement of eye drops from an ophthalmic medication containing bottle. The device of the present invention is designed to be attached to the bottle at all times, including while in use. Furthermore, the present invention is specifically designed to aid in the easy removal and replacement of ophthalmic solution containing bottle caps. The present invention, in its most basic form, comprises an eye ring, a bottle attaching portion and a flexible extension connecting the eye ring to the bottle attaching portion, wherein the eye ring and flexible extension may be moved off of the bottle axis to permit easy removal and replacement of the bottle cap.

13 Claims, 4 Drawing Sheets

EYE DROPPER POSITIONING DEVICE

FIELD OF THE INVENTION

The present invention relates to the ophthalmic solution dispensing devices, and has particular reference to a novel construction for an eye dropper positioning guide which works in combination with an ophthalmic medicant bottle, which includes a dispensing nozzle.

BACKGROUND

A common malady which affects eyes is that they become irritated due to dust and small foreign objects which are common pollutants in the air. One method for alleviating this irritation is the application of an eyewash, a liquid medicant, to the eyes. Most eyewashes are contained in a bottle which incorporates a dropper mechanism in the top. However, these eye droppers are difficult to operate. Most people have difficulty in applying drops due to the extreme sensitivity of their eyes. Moreover, poor vision makes it difficult to properly position or align an eye dropper bottle relative to the eye frequently causes drops to be improperly applied. Thus, the user quite often wastes eyewash by missing the intended eyeball.

Thus applying eye drops is generally difficult, uncomfortable and resulting in little, if any, of each drop entering the eye so that several attempts are necessary to insure placement of the ophthalmic solution in the eye. As a result, considerable amounts of the solution are wasted with no real assurance that a prescribed or desired amount of solution was placed in the eye.

Another common and potentially injurious problem occurs when the applicator tip accidentally comes in contact with the corneal surface. This problem is especially serious in individuals with physical or neurological limitations causing unsteady hand movements.

Generally, there is a line of eye drop guiding devices which may be attached to bottles containing ophthalmic medication. These bottles consist primarily of a fluid containing portion, a neck, a fluid dispensing portion and a bottle cap. The available devices, basically, are comprised of a bottle attaching portion, an eye ring, and some form of extension piece connecting the bottle attaching portion to the eye ring. However, these devices are constructed more with the actual end use of the device in mind, and not with the convenience and functionality of pre and post usage.

One difficulty with using the available eye drop guides is removing the cap of the attached bottle. The extension pieces of these devices are of rigid, unyielding construction and one would have to have the manual dexterity of a magician to comfortably remove the bottle cap without first removing the eye drop guide from the bottle.

Therefore, it is the primary purpose of the present invention to provide a simplified and easily attached add-on device which works in combination with existing eyedroppers to guide the user in properly placing ophthalmic medication. It is a further purpose of the present invention to provide an eye drop guide device which facilitates the removal of a bottle cap prior to use and while the device is simultaneously attached to the bottle.

PRIOR ART

The prior art reveals several different styles of eye drop directing apparatus. These range from replacement caps including special features to bottle attachments which hold the eyelid in place while simultaneously guiding the eye drops into the eye.

U.S. Pat. No. 5,387,202, by Baron, shows an eye drop dispensing device which consists essentially of a flexible tube of oval cross section which is placed over the body of a pliable ophthalmic solution container. Located at the base of the oval tube is a rim to aid in holding an eyelid in place during the application of the medication. The tube, and the enclosed pliable ophthalmic solution bottle, is simultaneously squeezed to apply the solution to the eye while the user is looking along the oval channel of the device. This device must be repeatedly removed and reattached in order to access the bottle cap.

U.S. Pat. No. 3,872,866, by Lelicoff, teaches a device which includes a ring for attaching the device to a bottle, an end piece for engaging a user's eyelid during the application of ophthalmic solution, and an inwardly curved extension piece attached to a boss on the ring. The curved extension piece is designed to aid in the placement of applied drops of medicated solution. The eye engaging portion of this device interferes with easy removal of the bottle cap.

U.S. Pat. Nos. 4,834,727 and 4,960,407, both by Cope, disclose a series of eye dropper bottle attachments. All of the embodiments utilize an oval eye lid retaining ring. The bottle is attached to the ring by either a single extension piece or a set of two extension pieces. The primary differences in the several embodiments of these two patents lies in the many different ways in which the device is attached to a bottle. One embodiment illustrates a split ring configuration wherein a ring is bisected to create two arcuate pieces, each attached to a separate extension piece. A second embodiment is a hook ring attachment wherein the hook grasps the bottle at the neck of the bottle. This hook attachment is attached to the eyelid ring by a single rigid extension piece. Another embodiment of these patents is an oval eyelid ring which is attached by two rigid extension poles to the neck ring of the device. A final embodiment illustrated by these patents shows the attachment of a singular oval eyelid ring to the neck ring by an extendible rigid extension piece. All of the embodiments of these patents have rigid extension pieces. Furthermore, their very design interferes with easy access to the bottle cap.

While these patents accomplish many fine results, they do not address the problem of removal and replacement of the cap of the ophthalmic solution containing bottle. The above eye drop guiding devices all include rigid extension pieces and eyelid grasping attachments which are located in close proximity to the cap of the bottle. The close location of these features makes it difficult to remove the bottle cap before use and replace the cap after use. This impediment to removal and replacement of the bottle cap frustrates the user and encourages the user to leave the cap off, thus creating a potentially unsanitary condition within the bottle containing ophthalmic solution.

SUMMARY OF THE INVENTION

It is an object of the present invention to provide an instrument which is easily and quickly attached to a plastic eye dropper bottle to increase accuracy in dispensing ophthalmic solutions in post-surgical and general use.

It is another object of the present invention to provide a device which allows for the easy removal and replacement of a bottle cap while the device is attached to the bottle.

It is still yet another object of the present invention to provide a device which includes a positioning indicator for the proper placement of an eye drop guide when attaching the guide to a bottle containing ophthalmic solution.

It is a further object of the present invention to provide a device which includes a flexible extension portion which allows the user to easily remove and replace the cap of a bottle by displacing the eyelid engaging ring off axis from the bottle.

It is still a further object of the present invention to provide a method for easy removal and replacement of a bottle cap while an eye drop guiding device is attached to the bottle.

BRIEF DESCRIPTION OF THE DRAWINGS

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings wherein:

DESCRIPTION OF PREFERRED EMBODIMENTS

Referring now to the figures, the present invention provides an eye drop guidance device which, when attached to a bottle with a cap, allows easy removal and replacement of the cap. The device of the present invention is simpler to construct and especially simpler to use than any devices thus discovered in the prior art. This simplicity is especially evident when it is understood that the device of the present invention may not only be used with two hands as all eye drop positions guides are, but with a single hand, if necessary. This feat is nearly impossible of many of the prior art devices.

Figure 1:
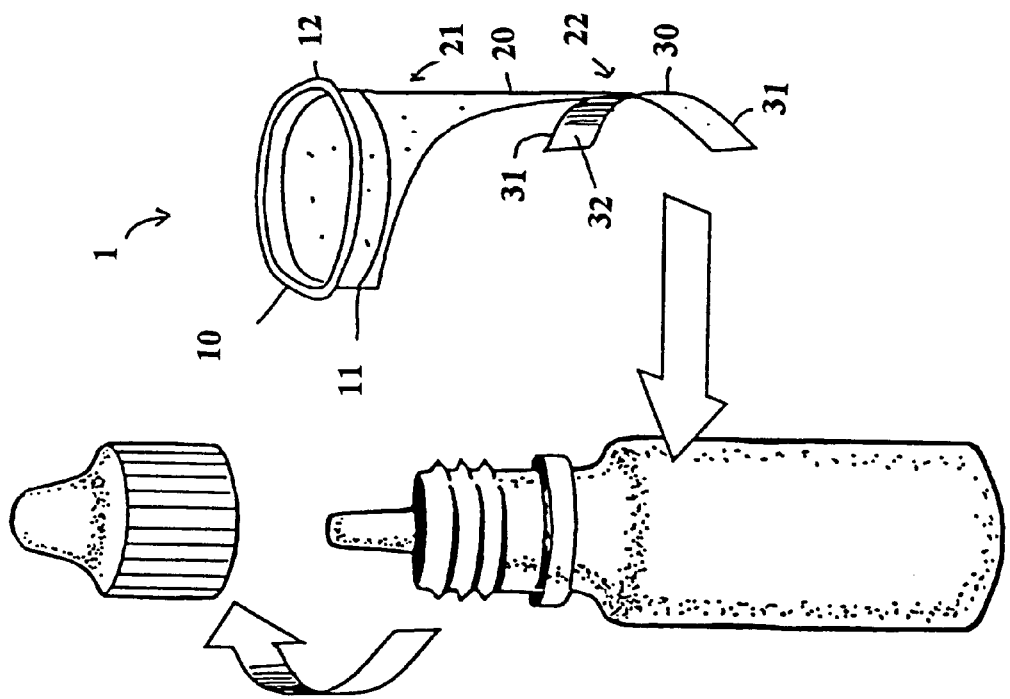
FIG. 1 illustrates the attachment of a first embodiment of the present invention to a bottle containing ophthalmic solution.

FIG. 1 illustrates a first preferred embodiment 1 of the present invention. The device has an oval, or rounded rectangular eyelid engaging ring 10. The ring 10 has a support flange 11 attached to a back side and which runs along the entire periphery of the ring. A flexible extension piece 20 is attached to the support flange 11 at a first end 21. The flexible extension piece 20 is preferably made from a thin, flexible plastic material. The extension piece 20 is preferably attached along a long side 12 of the oval shape of the eyelid engaging ring 10. Furthermore there is, attached at a second end 22 of the extension piece 20, a bottle attaching portion 30. As can be seen from FIG. 1, the bottle attaching portion 30 of the first preferred embodiment 1 comprises a pair of arms 31 extending transverse to the direction of the extension piece 20 at opposite sides 23 of the extension piece 20. Applied to an inner surface 32 of the pair of arms 31, and on an inner surface 24 of a portion of the second end 22 of the extension piece 20, is adhesive. The adhesive is protected from pre-use contamination by a thin covering 33, typically paper or a wax paper material. Finally, there are position indicators 35 placed on either an inside or outside surface of the device 1. By selecting a clear plastic material, neither inside or outside surface is preferable over the other.

Figure 1B:
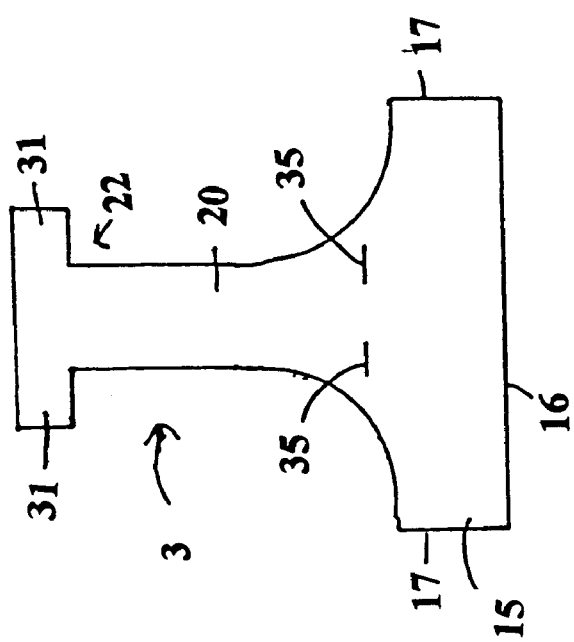
FIG. 1B depicts the shape of thin flexible plastic used to construct the first preferred embodiment.

One method of constructing the first preferred embodiment 1 is to take a piece of thin flexible plastic material and cut a shape 3 as illustrated in FIG. 1B. On the shape is a substantially rectangular base portion 15. One long side of the base portion 15 gradually extends outward to form the extension piece 20. When looking at the base portion 15 and extension piece 20, they appear to form a T-shape wherein the junction of the T is a smooth and continuous curve, as opposed to discontinuous. The extension piece 20 has at the second end 22, two small rectangular arms 31 projecting transverse to the long direction of the extension piece 20. The eyelid engaging ring 10 is formed by rolling a lower end 16 of the base 15, preferably with the roll directed to an outside surface of the plastic material. The roll does not consume the entire width of the base portion 15, since eyelid engaging ring 10. Opposite outside ends 17 of the base 15 are then attached to each other to form the ring 10 itself. The position indicators 35 are then placed on the extension piece 20 or the support flange 11 at a position where the dispensing end of a bottle should be located. Alternately, device 1 may be manufactured by injection molding techniques or other similar plastic shaping technologies.

When using the first preferred embodiment 1, the user will remove the protective covering 33 from the applied adhesive. The user will then align the bottle to the device 1 with the position indicators such that the tip of the dispensing portion of the bottle is properly placed relative to the eyelid engaging ring 10. The user then firmly applies the attaching section 30, with the adhesive located on the inside, to the bottle. This, then, firmly attaches the first preferred embodiment 1 to the bottle.

Figure 2:
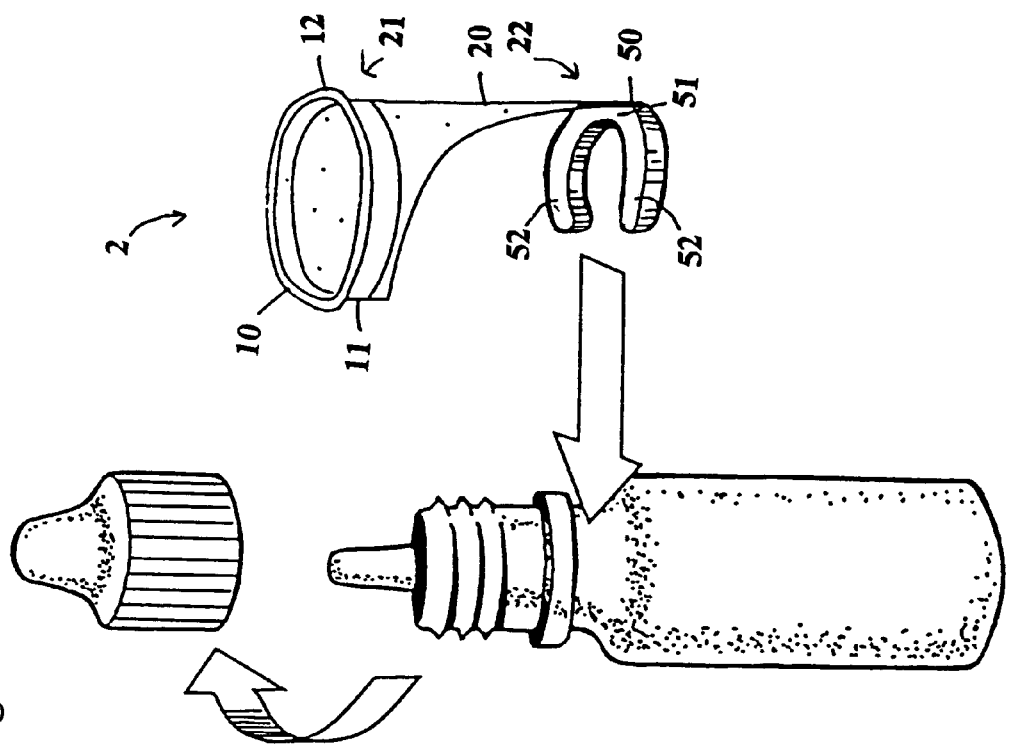
FIG. 2 illustrates the attachment of a second embodiment of the present invention to a bottle containing ophthalmic solution.

FIG. 2 illustrates a second preferred embodiment 2. The device of the second preferred embodiment 2 also has an oblong, or rounded rectangular eyelid engaging ring 10. The ring 10 has a support flange 11 attached to a back side and which runs along the entire periphery of the ring 10. A flexible extension piece 20 is attached to the support flange 11 at a first end 21 of the extension piece 20. The flexible extension piece 20 is preferably made from a thin, flexible plastic material. The extension piece 20 should be attached along a long side 12 of the oval shape of the eyelid engaging ring 10. Furthermore there is, attached at a second end 22 of the extension piece 20, a bottle attaching portion 50. As can be seen from FIG. 2, the bottle attaching portion 50 of the second preferred embodiment 2 is a C-shaped semi-rigid piece of plastic. The C-shaped bottle attaching portion 50 is formed by a thickened base portion 51 with a pair of inwardly curved arms 52 attached at opposite ends 53 of the base portion 51. The base portion 51 is attached to an inner surface 24 of the extension piece at a back side of the base portion 51.

Figure 2B:
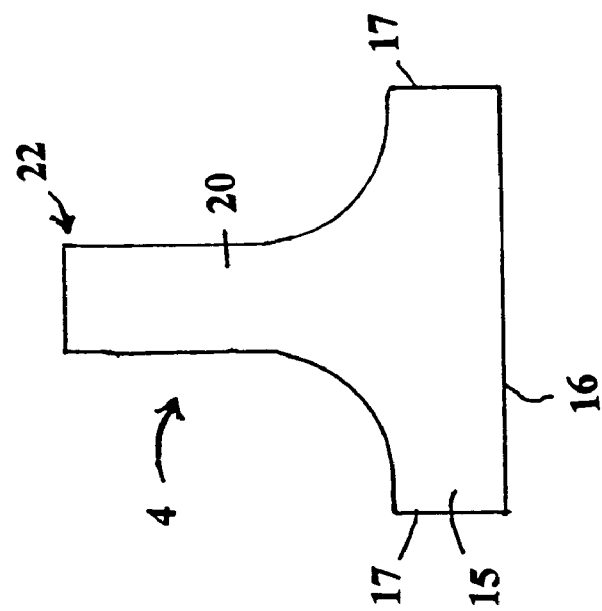
FIG. 2B depicts the shape of thin flexible plastic used to construct the second referred embodiment.

One method of constructing the second preferred embodiment 2 is to take a piece of thin flexible plastic material and cut a T-shape 4 as illustrated in FIG. 2B. The T-shape comprises a substantially rectangular base portion 15. One long side of the base portion 15 gradually extends outward to form the extension piece 20. When looking at the base portion 15 and extension piece 20, the junction of the T form a smooth and continuous curve, as opposed to discontinuous. The eyelid engaging ring 10 is formed by rolling a lower end 16 of the base 15, preferably with the roll directed to an outside surface of the plastic material. The roll does not consume the entire width of the base portion 15, since the unused portion forms the support flange 11 which runs along the periphery of the eyelid engaging ring 10. Opposite outside ends 17 of the base 15 are then attached to each other to form the ring 10 itself. Alternately, device 2 may be manufactured by injection molding techniques or other similar plastic shaping technologies.

In use, as illustrated in FIG. 2, the bottle attaching piece 50 is simply clipped onto an area of the ophthalmic solution containing bottle near the neck. The semi-rigidity of the C-shaped bottle attaching portion 50 is necessary to allow repeated attachment and removal of the device from the bottle. The cap of the bottle may then be removed and replaced as described above in the first preferred embodiment.

Figure 3:
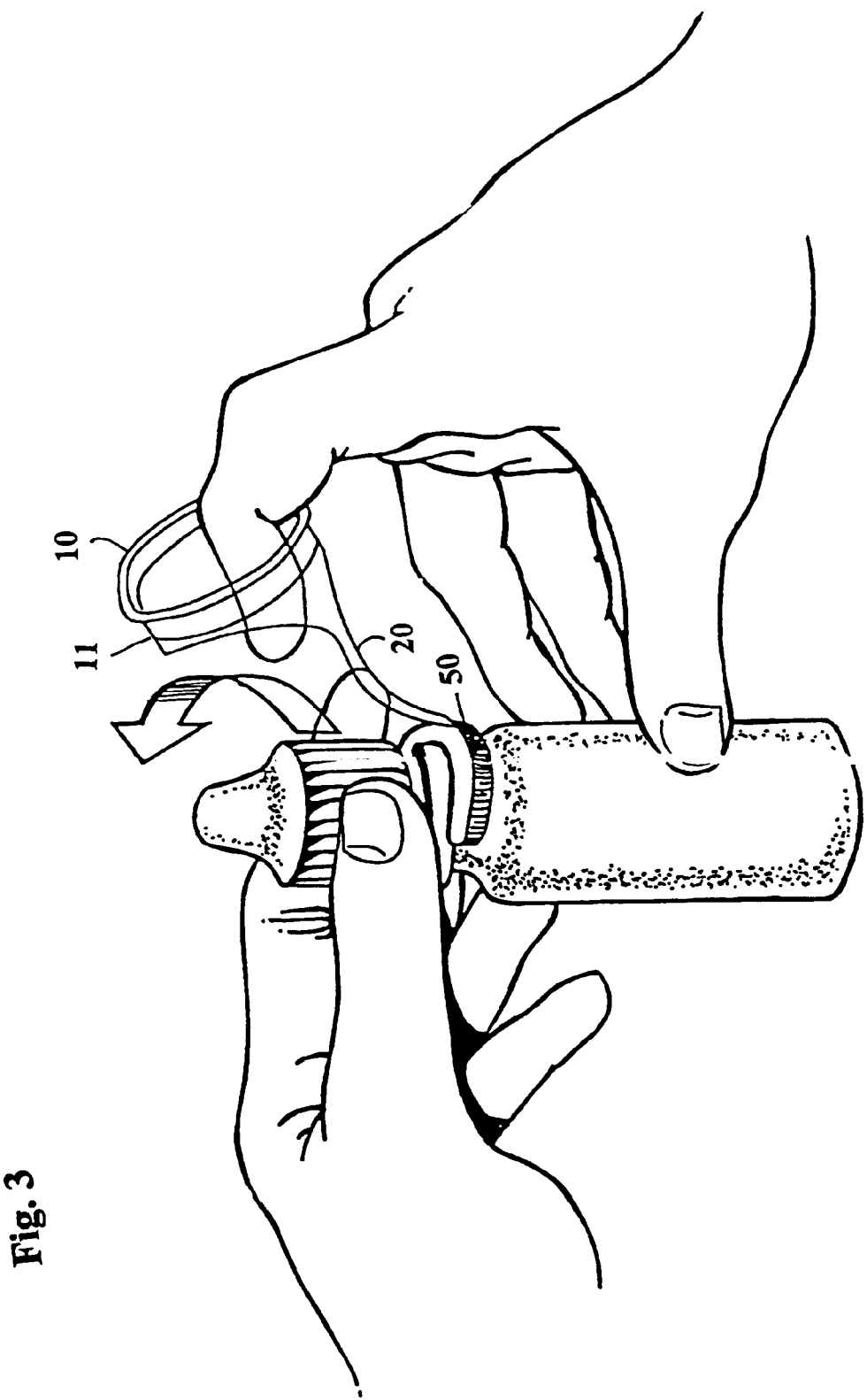
FIG. 3 depicts the removal of a bottle cap by displacing the eyelid engaging ring from the bottle axis.

In order to use the bottle with the device 1 or 2 attached, the user will grasp the bottle in a first hand with the bottle oriented in an upward position. The user then grasps the eyelid retaining ring 10 with a finger of the first hand, frequently this will be the index finger. The user then pulls back on the eyelid retaining ring 10 with the finger, thus displacing the ring 10 from axial alignment with the bottle. This displacement temporarily removes the obstructive effect of the extension piece 20 and eyelid retaining piece 10. The user may then remove the bottle cap with a second hand. Once the bottle cap is removed, the eyelid retaining ring 10 may then be allowed to regain its former position by releasing the finger grasp, thus causing the flexible extension piece 20 to automatically return to the desired alignment with the applicator tip of the bottle. This is illustrated in FIG. 3.

Figure 4:
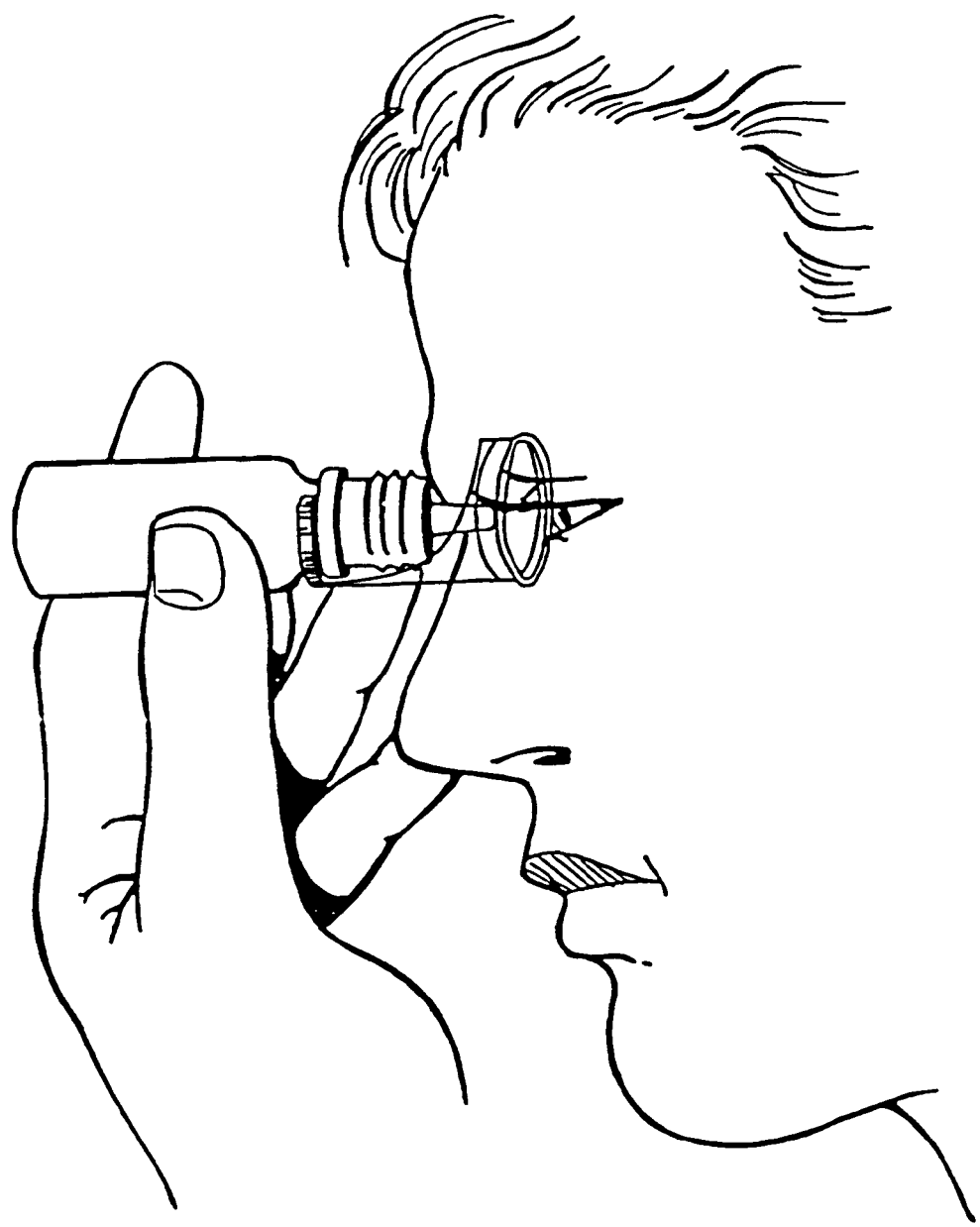
FIG. 4 shows the device guiding eye drops into an eye of a user.

The eyelid retaining ring 10 is then placed over the eye, preferably with a portion of the ring 10 frictionally holding the eyelid in an open position. The head is then tilted backward and the user gazes upward at the dispensing portion of the bottle. The bottle is gently squeezed, thereby applying an amount of ophthalmic solution onto the eye. See FIG. 4.

Once the solution is applied, the bottle and attached device 1 or 2 may then be removed, and once again placed into an upright position. The user then, holding the bottle in the first hand, once again grasps the eyelid retaining ring 10 with the finger and displaces the ring off axis of the bottle. The second hand then replaces the bottle cap. The eyelid retaining ring 10 is finally, once again, allowed to regain its original position by releasing the finger's grasp.

It is easy to see from the above descriptions that the device of the present invention is simpler to manufacture and use than previous devices. Additionally, the device may be held in a single hand, the eye ring retaining ring 10 displaced with the index finger of the singe hand and the bottle cap removed and replace with remaining fingers of the single hand. This thus demonstrates part of the simplicity of the present invention.

While these descriptions directly describe the above embodiments, it is understood that those skilled in the art may conceive modifications and/or variations to the specific embodiments shown and described herein. Any such modifications or variations which fall within the purview of this description are intended to be included therein as well. It is understood that the description herein are intended to be illustrative only and not intended to be limitative. Rather, the scope of the invention described herein is limited only by the claims appended hereto.

What is claimed is:

1. A device for applying ophthalmic solutions comprising:
   a) an eye guide;
   b) a flexible extension portion attached to the eye guide, where the flexible extension portion is resiliently bendable such that a transverse force applied to the eye guide moves the eye guide significantly out of place and the eye guide returns to its original position once the transverse force is removed; and
   c) a bottle attaching portion which is capable of fastening to a bottle, attached to a second end of the extension portion, wherein the bottle attaching portion further comprises a base portion attached to the flexible extension portion and two arms with inwardly curved distal ends, wherein the bottle attaching portion is clipped onto a neck portion of the bottle.

2. A device as in claim 1 wherein the eye guide is an oval ring.

3. A device as in claim 2 wherein the eye guide further has a support flange attached to a back surface of the eye guide.

4. A device as in claim 3 wherein the flexible extension portion is a thin sheet of plastomer.

5. A device as in claim 1 wherein the bottle attaching portion further comprises a thin flexible portion with an adhesive applied to an inner side, wherein the bottle attaching portion is adapted to be attached to a bottle by contacting the applied adhesive to a surface of the bottle.

6. A device as in claim 1 wherein the eye guide is an oval ring, the flexible extension portion further comprises a thin sheet of plastomer, and the bottle attaching portion is a thin flexible portion comprising two arms extending transverse to the extension portion, said bottle attaching portion further having an adhesive applied to an inner surface for the attachment to a neck portion of a bottle.

7. A device in claim 1 wherein the eye guide is an oval ring the flexible extension portion further comprises a thin sheet of plastomer, and the bottle attaching portion is further comprised of a base portion with two arms attached at opposite ends of the base portion, said arms further being inwardly curved at their respective distal ends, wherein the arms are adapted to grasp a neck portion of a bottle.

8. A device as in claim 6 wherein the flexible extension portion is attached along a long side of the oval eye guide.

9. A device as in claim 7 wherein the flexible extension portion is attached along a long side of the oval eye guide.

10. A method for applying ophthalmic solutions by:
    a) attaching a bottle guide which is comprised of an eye guide, a flexible extension portion attached at a first end to the eye guide, where the flexible extension portion is resiliently bendable such that a transverse force applied to the eye guide moves the eye guide significantly out of place and the eye guide returns to its original position once the transverse force is removed, and a bottle attaching portion, which is capable of fastening to a bottle, attached to a second end of the flexible extension portion, said bottle attaching portion further being fastened to a bottle with a cap containing ophthalmic solution;
    b) placing the eye guide around an eye contained in a head;
    c) tilting the head backward and looking up at a dispensing portion of the bottle;
    d) gently applying drops of ophthalmic solution to the eye; and
    e) removing the bottle guide from the proximity of the face.

11. A method as in claim 10 further comprising the steps of removing the bottle cap by:
   a) grasping the bottle in a first hand;
   b) grasping the eye guide with a finger of the first hand;
   c) pulling the eye guide away from axial alignment with the bottle with the finger of the first hand;
   d) removing the cap of the bottle with a second hand; and
   e) allowing the eye guide to regain axial alignment with the bottle by releasing the eye guide.

12. A method as in claim 10 further comprising the steps of replacing the bottle cap by:
   a) grasping the eye bottle in the first hand;
   b) grasping the eye guide with the finger of the first and
   c) pulling the eye guide away from axial alignment with the bottle with the finger of the first hand;
   d) replacing the cap onto the bottle with the second hand; and
   e) allowing the eye guide to regain axial alignment with the bottle by releasing the eye guide.

13. A method as in claim 10 further comprising the removal of the bottle cap prior to use by
   a) grasping the bottle in a first hand;
   b) grasping the eye guide with a finger of the first hand;
   c) pulling the eye guide away from axial alignment with the bottle with the finger of the first hand;
   d) removing the cap of the bottle with a second hand; and
   e) allowing the eye guide to regain axial alignment with the bottle by releasing the eye guide; and replacement of the bottle cap after use by
   a) grasping the eye bottle in the first hand;
   b) grasping the eye guide with the finger of the first and
   c) pulling the eye guide away from axial alignment with the bottle with the finger of the first hand;
   d) replacing the cap onto the bottle with the second hand; and
   e) allowing the eye guide to regain axial alignment with the bottle by releasing the eye guide.

* * * * *